(12) United States Patent
Sadohara et al.

(10) Patent No.: US 10,533,022 B2
(45) Date of Patent: Jan. 14, 2020

(54) SILICON OLIGOMER AND PRODUCTION METHOD THEREFOR

(71) Applicant: JCU CORPORATION, Taito-ku (JP)

(72) Inventors: Daisuke Sadohara, Tokyo (JP); Kenichi Nishikawa, Kanagawa (JP); Yasutake Nemichi, Kanagawa (JP); Hisayuki Toda, Kanagawa (JP); Hiroki Yasuda, Kanagawa (JP); Shinsuke Takagi, Kanagawa (JP); Christopher Ernest John Cordonier, Kanagawa (JP)

(73) Assignee: JCU CORPORATION, Taito-ku (JP)

(*) Notice: Subject to any disclaimer, the term of this patent is extended or adjusted under 35 U.S.C. 154(b) by 0 days.

(21) Appl. No.: 15/699,714

(22) Filed: Sep. 8, 2017

(65) Prior Publication Data

US 2017/0369513 A1    Dec. 28, 2017

Related U.S. Application Data

(63) Continuation of application No. 14/901,148, filed as application No. PCT/JP2013/067778 on Jun. 28, 2013, now abandoned.

(51) Int. Cl.
  *C07F 7/04* (2006.01)
  *C08G 77/02* (2006.01)
  *C09D 183/00* (2006.01)

(52) U.S. Cl.
  CPC ............... *C07F 7/04* (2013.01); *C08G 77/02* (2013.01); *C09D 183/00* (2013.01)

(58) Field of Classification Search
  CPC .................................................. C07F 7/04
  USPC ................................................. 528/425, 20
  See application file for complete search history.

(56) References Cited

U.S. PATENT DOCUMENTS

| | | | |
|---|---|---|---|
| 3,029,269 | A | 4/1962 | Abbott et al. |
| 2006/0189711 | A1 | 8/2006 | Ng |
| 2008/0194726 | A1 | 8/2008 | Ng |
| 2009/0131585 | A1 | 5/2009 | Prasse |
| 2009/0149554 | A1 | 6/2009 | Ishikawa et al. |
| 2010/0016622 | A1 | 1/2010 | Ng |
| 2011/0166283 | A1 | 7/2011 | Prasse |

FOREIGN PATENT DOCUMENTS

| | | |
|---|---|---|
| CN | 85 1 03438 | 10/1986 |
| CN | 101243094 A | 8/2008 |
| JP | 2007 70353 | 3/2007 |
| JP | 2008 163335 | 7/2008 |
| JP | 2008 531787 | 8/2008 |

OTHER PUBLICATIONS

International Search Report dated Aug. 13, 2013 in PCT/JP2013/067778 filed Jun. 28, 2013.
Abbott, Doyle A. et al., "Silicate Esters and Related Compounds", Journal of Chemical and Engineering Data, vol. 6, No. 3, pp. 437-442, 1961.
Iwamoto, K. et al., "Preparation of Specialty Inorganic-Organic Composite Materials by Sol-Gel Process", UDC 678.029.4 : 666.1.037.6, vol. 42, No. 8, pp. 466-473, 1990.
Office Action dated Jun. 1, 2017, in Chinese Patent Application No. AZ 201380077750.2 (with English Translation).

*Primary Examiner* — Duc Truong
(74) *Attorney, Agent, or Firm* — Oblon, McClelland, Maier & Neustadt, L.L.P.

(57) ABSTRACT

An object of the present invention is to provide a silicon oligomer having a novel function that has not been achieved by a conventional condensation product of water and a tetraalkoxysilane. Provided are a silicon oligomer represented by the following formula (I) and a production method therefor:

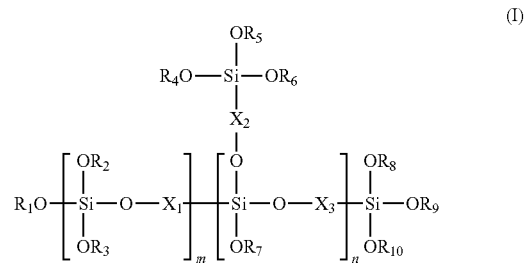

(I)

wherein $R_1$ to $R_{10}$ each independently is an alkyl group or a hydroxyalkyl group, each having 1 to 4 carbon atoms; $X_1$ to $X_3$ each independently is a group represented by the following formula (II); n is 0 or 1; and m is an integer of 1 to 3 when n is 0, and m is 1 when n is 1:

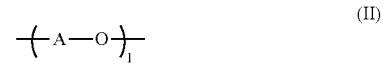

(II)

wherein A is an alkylene group having 2 to 4 carbon atoms which may be branched, and l is an integer of 1 to 3.

21 Claims, No Drawings

SILICON OLIGOMER AND PRODUCTION METHOD THEREFOR

CROSS REFERENCE TO RELATED APPLICATIONS

This application is a Continuation of U.S. application Ser. No. 14/901,148, filed Dec. 28, 2015, which is a 371 of PCT/JP13/67778, filed Jun. 28, 2013, the text of which is hereby incorporated by reference.

TECHNICAL FIELD

The present invention relates to a novel silicon oligomer, more particularly to a novel silicon oligomer and a method for producing the same.

BACKGROUND ART

There have been a number of reports on a method in which a film is formed using a condensation product of water and a tetraalkoxysilane, and a member to be treated is subjected to inorganic-organic hybrid coating with the film (NPL 1).

However, the above-mentioned condensation product has a small distance between the poles of silicon atoms, and hence poses a problem in that a film obtained by applying the condensation product and heating it is rigid. Especially when this film is formed on a fastening member, it has been difficult to achieve both a corrosion resistance and a function, such as a coefficient of friction, at the same time.

Further, a coating liquid containing the above condensation product has a problem about the stability, for example, a problem in that a hydrolysis proceeds with the passage of time, so that the coating liquid cannot keep the sol-gel properties.

CITATION LIST

Non Patent Literature

NPL 1: Kazutoshi Iwamoto et. al., "Functionalization of inorganic-organic hybrid materials by sol-gel method", Seisan Kenkyu, Vol. 42, No. 8, p. 466 to 473, 1990

SUMMARY OF INVENTION

Technical Problem

A task of the present invention is to provide a silicon oligomer which can solve the above-mentioned problems, and which has a novel function that has not been achieved by a conventional condensation product of water and a tetraalkoxysilane.

Solution to Problem

The present inventors have conducted extensive and intensive studies with a view toward solving the above-mentioned problems. As a result, it has been found that, by reacting a tetraalkoxysilane having a specific structure and a dihydric alcohol having a specific structure with each other, a novel silicon oligomer having a large distance between the poles of silicon atoms can be obtained. Further, it has been found that when a member is treated with a coating agent using the above silicon oligomer, it is possible to impart a corrosion resistance and a function to the member treated, and the present invention has been completed.

Specifically, the invention is the following (1) to (6).

(1) A silicon oligomer represented by the following formula (I):

$$R_4O-\underset{\underset{X_2}{|}}{\overset{\overset{OR_5}{|}}{Si}}-OR_6 \quad (I)$$

$$R_1O\left[\underset{\underset{OR_3}{|}}{\overset{\overset{OR_2}{|}}{Si}}-O-X_1\right]_m\left[\underset{\underset{OR_7}{|}}{\overset{\overset{O}{|}}{Si}}-O-X_3\right]_n\underset{\underset{OR_{10}}{|}}{\overset{\overset{OR_8}{|}}{Si}}-OR_9$$

wherein $R_1$ to $R_{10}$ each independently is an alkyl group or a hydroxyalkyl group, each having 1 to 4 carbon atoms; $X_1$ to $X_3$ each independently is a group represented by the following formula (II); n is 0 or 1; and m is an integer of 1 to 3 when n is 0, and m is 1 when n is 1:

$$-\!\!\left(\!A\!-\!O\!\right)_{\!l}\!\!- \quad (II)$$

wherein A is an alkylene group having 2 to 4 carbon atoms, which may be branched, and l is an integer of 1 to 3.

(2) A polymerizable product which is obtained by heating the above-mentioned silicon oligomer.

(3) A method for producing the above silicon oligomer, which includes reacting a tetraalkoxysilane represented by the following formula (III) and a dihydric alcohol represented by the following formula (IV) with each other in the presence of a metal catalyst, an acid, or an alkali:

$$R_{11}O-\underset{\underset{OR_{13}}{|}}{\overset{\overset{OR_{12}}{|}}{Si}}-OR_{14} \quad (III)$$

wherein $R_{11}$ to $R_{14}$ each independently is an alkyl group or a hydroxyalkyl group, each having 1 to 4 carbon atoms, and $$HO\!\!\left(\!B\!-\!O\!\right)_{\!k}\!\!H \quad (IV)$$

wherein B is an alkylene group having 2 to 4 carbon atoms, which may be branched, and k is an integer of 1 to 3.

(4) A coating agent containing the above-mentioned silicon oligomer.

(5) A surface treating method characterized by treating a member to be treated with the above-mentioned coating agent.

(6) A surface treated product, which is obtained by treating a member to be treated with the above coating agent.

Advantageous Effects of Invention

The silicon oligomer of the invention has excellent resistance to hydrolysis in coexistence with water, as compared to a conventional silicon oligomer.

The method for producing the silicon oligomer of the invention is a method which needs no operation for separation or purification, and which can provide an oligomer with ease and high reproducibility.

Further, a coating agent containing the silicon oligomer of the invention is advantageous in that the raw material oligomer per se can be dissolved in a solvent including water, and therefore is easily processed into a water-soluble coating and has excellent handling properties.

Furthermore, when a member is treated with the coating agent containing the silicon oligomer of the invention, it is possible to impart a corrosion resistance and a function, such as a high coefficient of friction, to the member treated.

DESCRIPTION OF EMBODIMENTS

The silicon oligomer of the invention is a silicon oligomer represented by the following formula (I).

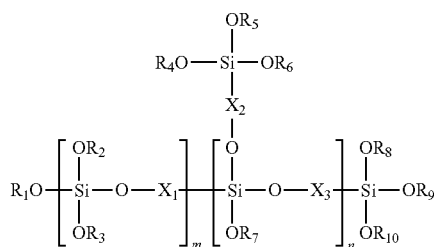

In the above formula (I), $R_1$ to $R_{10}$ each independently is an alkyl group or a hydroxyalkyl group, each having 1 to 4 carbon atoms, preferably an alkyl group or a hydroxyalkyl group, each having 2 carbon atoms, more preferably a hydroxyalkyl group having 2 carbon atoms.

Further, in the above formula (I), $X_1$ to $K_3$ each independently is represented by the following formula (II).

In the above formula (II), A is an alkylene group having 2 to 4 carbon atoms which may be branched, preferably an ethylene group, a propylene group or a butylene group, more preferably an ethylene group, and l is an integer of 1 to 3, preferably 1.

Further, in the above formula (I), n is 0 or 1, and m is an integer of 1 to 3 when n is 0, and m is 1 when n is 1, preferably n is 0 and m is 1.

As an especially preferred embodiment of the silicon oligomer of the invention, there can be mentioned one which is represented by the following formula (V).

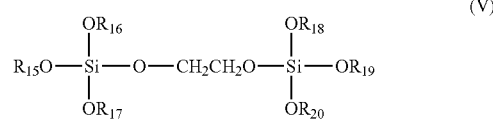

In the above formula (V), $R_{15}$ to $R_{20}$ each independently is an ethyl group or a hydroxyethyl group, and preferably all of $R_{15}$ to $R_{20}$ are an ethyl group or a hydroxyethyl group.

The method for producing the silicon oligomer of the invention (hereinafter, referred to as "the method of the invention") is not particularly limited, but, for example, the silicon oligomer can be obtained by reacting a tetraalkoxysilane represented by the following formula (III):

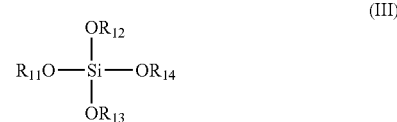

and a dihydric alcohol represented by the following formula (IV):

with each other in the presence of a metal catalyst, an acid, or an alkali, preferably in the presence of a metal catalyst.

Further, when an alcohol formed during the reaction is not subjected to fractional distillation, the polymerization reaction is advantageously controlled. When a solid resin catalyst conventionally used in the polymerization reaction of a tetraalkoxysilane, or the like is used, it is difficult to control the polymerization reaction, and therefore the silicon oligomer represented by the above formula (I) cannot be obtained.

In the tetraalkoxysilane represented by the above formula (III), $R_{11}$ to $R_{14}$ each independently is an alkyl group or a hydroxyalkyl group, each having 1 to 4 carbon atoms, preferably an alkyl group or a hydroxyalkyl group, each having 2 carbon atoms, more preferably a hydroxyalkyl group having 2 carbon atoms. One type of or two or more types of the tetraalkoxysilanes represented by the formula (III) may be used.

In the dihydric alcohol represented by the above formula (IV), B is an alkylene group having 2 to 4 carbon atoms which may be branched, preferably an alkylene group having 2 carbon atoms, and k is an integer of 1 to 3, preferably 1. Specific examples of the dihydric alcohols represented by the formula (IV) include ethylene glycol, propylene glycol, butylene glycol, diethylene glycol, and triethylene glycol, and, of these, preferred are ethylene glycol, propylene glycol, and butylene glycol. One type of or two or more types of the dihydric alcohols represented by the formula (IV) may be used.

In the method of the invention, with respect to the metal catalyst present during the reaction, there is no particular limitation as long as it contains a metal having catalytic activity, and examples include ones containing aluminum, cobalt, titanium, zinc, molybdenum, tin, or the like, and preferred examples include ones containing aluminum, cobalt, or titanium. Specific examples of metal catalysts include aluminum salts, such as aluminum chloride, cobalt salts, such as cobalt chloride, and titanium salts, such as titanium trichloride, and preferred is aluminum chloride or the like. One type of or two or more types of these metal catalysts may be used. The metal catalyst is present in the state of being dissolved in the dihydric alcohol represented by the formula (IV) in the system during the reaction.

Further, in the method of the invention, as examples of acids present during the reaction, there can be mentioned inorganic acids, such as hydrochloric acid, sulfuric acid, and nitric acid. The acid is present in the state of being dissolved in the dihydric alcohol represented by the formula (IV) in the system during the reaction.

Specifically, in the method of the invention, a metal catalyst, an acid, or an alkali is added to the dihydric alcohol represented by the formula (IV), and then the resultant mixture is heated to a reaction temperature while stirring, and further the tetraalkoxysilane represented by the formula (III) is added to the mixture to effect a reaction. The reaction temperature is 25 to 150° C., preferably 30 to 70° C., and the reaction time is 30 minutes to 8 hours, preferably 2 to 4 hours. It is important that the reaction is conducted so that the molar ratio of the tetraalkoxysilane represented by the formula (III) and the dihydric alcohol represented by the formula (IV) is 4:1 to 1:4, preferably 1:2 to 1:4. Thus, the dihydric alcohol represented by the formula (IV) is incorporated between the tetraalkoxysilane and another tetraalkoxysilane, so that the distance between the poles of silicon atoms becomes longer.

The thus obtained silicon oligomer of the invention can be identified by a known method, such as $^1$H NMR, $^{29}$S1 NMR, IR, or MASS. Specifically, the silicon oligomer can be identified by $^1$H NMR and $^{29}$S1 NMR.

The silicon oligomer of the invention is a polymerizable substance which undergoes polymerization due to heating or the like to obtain a polymerizable product. Further, the silicon oligomer of the invention has a property of being dissolved in a solvent, such as water, isopropyl alcohol, or ethyl cellosolve, or a mixed solvent thereof.

When the silicon oligomer of the invention is in the form of being diluted with, for example, a glycol solvent, such as polyethylene glycol or ethyl cellosolve, the silicon oligomer can be stably stored even in the presence of water. Especially when using polyethylene glycol 200 to 1,000, preferably polyethylene glycol 200 as a glycol solvent for diluting the silicon oligomer, the silicon oligomer can be stably stored for a long term even in the presence of water.

The silicon oligomer of the invention has the above-mentioned property, and further can be used like a conventionally known silicon oligomer in applications of a surface treatment agent and the like.

Further, a polymerizable product can be obtained by heating the silicon oligomer of the invention as such, and thus a film having flexibility can be formed from the product. Therefore, utilizing this property, the silicon oligomer of the invention is preferably used in a coating agent, particularly a coating agent for a fastening member.

With respect to the coating agent containing the silicon oligomer of the invention (hereinafter, referred to as "the coating agent in the invention"), there is no particular limitation as long as the coating agent contains the silicon oligomer of the invention, and, for example, the coating agent may contain one member or two or more members selected from the group consisting of a resin, a colorant, a friction coefficient adjustor, and a film-forming agent which are added to a conventionally known coating agent. The coating agent can be prepared by appropriately stirring and mixing together the above-mentioned components.

With respect to the resin used in the coating agent in the invention, there is no particular limitation as long as it is soluble or dispersible in the coating agent, and, for example, there can be mentioned acrylic resins, urethane resins, phenolic resins, and epoxy resins. Of these resins, acrylic resins are preferred, an alkyl methacrylate copolymer, a colloidal silica-acryl composite, and an ethylene-acrylic acid copolymer ammonium salt are more preferred, and an alkyl methacrylate copolymer is especially preferred. One type of or two or more types of these resins can be used. The resin is incorporated into the coating agent in an amount of 0.1 to 50%, preferably 1 to 20%.

With respect to the colorant used in the coating agent in the invention, there is no particular limitation as long as it is soluble or dispersible in the coating agent, and, for example, there can be mentioned dye colorants and pigment colorants. One type of or two or more types of these colorants can be used. The colorant is incorporated into the coating agent in an amount of 0.1 to 50%, preferably 1 to 30%.

Further, with respect to the friction coefficient adjustor used in the coating agent in the invention, there is no particular limitation as long as it is soluble or dispersible in the coating agent, and, for example, there can be mentioned polyolefin compounds, such as polyethylene and polypropylene, and fluorine compounds, such as polytetrafluoroethylene (PTFE) and a tetrafluoroethylene-perfluoroalkyl vinyl ether copolymer (PFA). One type of or two or more types of these friction coefficient adjustors can be used. The friction coefficient adjustor is incorporated into the coating agent in an amount of 0.1 to 10%, preferably 0.5 to 5%.

Further, with respect to the film-forming agent used in the coating agent in the invention, there is no particular limitation as long as it is soluble or dispersible in the coating agent, and, for example, there can be mentioned colloidal silica and fumed silica. One type of or two or more types of these film-forming agents can be used. The film-forming agent is incorporated into the coating agent in an amount of 0.1 to 20%, preferably 1 to 10%.

Further, a component of an agent for imparting another function or the like can be incorporated into the coating agent in the invention in such an amount that the effects of the invention are not sacrificed.

A surface treatment for a member to be treated can be made by treating the member with the above-described coating agent in the invention.

Specifically, with respect to the member to be treated, the surface of the member to be treated may be formed from a metal and a resin, and the inside of the member may be formed from any material. Further, with respect to the shape of the member to be treated, there is no particular limitation.

Particularly, as examples of the members to be treated which can be treated with the coating agent in the invention, there can be mentioned members having a surface formed from the following (a) to (d), preferably from (b):

(a) magnesium or a magnesium alloy,
(b) zinc or a zinc alloy,
(c) a metal selected from the group consisting of iron, copper, nickel, cobalt, chromium, and tin, or an alloy containing the above two or more metals,
(d) a synthetic resin selected from the group consisting of an acrylonitrile-butadiene-styrene copolymer, a polycarbonate, bismaleimidetriazine, and a polyimide, or a synthetic resin alloy containing the above two or more resins.

The treatment of a member to be treated with the coating agent in the invention may be conducted by a similar method to a treatment method using a conventionally known coating agent, for example, in which a member to be treated is immersed in the coating agent in the invention, or the coating agent in the invention is sprayed onto a member to be treated, and, if necessary, the resultant member is subjected to heating or the like.

Specifically, when a member to be treated is immersed in the coating agent in the invention, for example, a dip-and-spinning method is preferred.

Further, specifically, when the coating agent in the invention is sprayed onto a member to be treated, for example, a spray coating method is preferred.

Further, the heating may be made by heating the member to a temperature equal to or higher than the temperature at which a film is formed, for example, 80° C. or higher, preferably 100 to 200° C.

After the heating, the resultant member may be further treated with the coating agent and heated to form a stacked structure.

The thus obtained product surface-treated with the coating agent in the invention has imparted thereto a corrosion resistance and a function. Therefore, the product can be advantageously used in applications of a fastening member and the like.

The corrosion resistance indicates a resistance to corrosion, and the function indicates friction coefficient adjustment. The corrosion resistance means that the white rust generation area is 7% or less, preferably 5% or less, more preferably 3% or less, as measured in a salt spray test performed in accordance with JIS Z 2371. The friction coefficient adjustment means suppression of the dispersion of the coefficient of friction of a film.

EXAMPLES

Hereinbelow, the present invention will be described in detail with reference to the following Examples, which should not be construed as limiting the scope of the invention.

Example 1

Preparation of a Silicon Oligomer:

To 336 g (5.4 mol) of ethylene glycol was added 1.8 g of aluminum chloride hexahydrate, and the resultant mixture was heated to 50° C. by means of a mantle heater while stirring, and 564 g (2.7 mol) of tetraethoxysilane (TEOS) was mixed into the mixture to effect a reaction for 2 hours without subjecting to fractional distillation of an alcohol formed during the substitution reaction. The temperature for the reaction was 50° C. or lower. Before the reaction, TEOS and ethylene glycol were not mixed with each other and suffered separation into two layers, but, after the reaction, they were changed to a single layer because TEOS was completely reacted. This means that the degree of reaction of TEOS is 100%.

After the reaction, cooling was performed to obtain a reaction product. Before and after the reaction, $^1$H NMR and $^{29}$Si NMR measurements were conducted. In the $^1$H NMR measurement, in the spectrum obtained after completion of the reaction, peaks ascribed to ethanol appeared around 1.1 and 3.5 ppm. It is considered that ethanol was formed as a result of the substitution reaction caused between the ethoxy group of TEOS and ethylene glycol.

In the $^{29}$Si NMR measurement, in the spectrum obtained before the reaction, only a single peak ascribed to TEOS appeared around −82 ppm, and, in the spectrum obtained after completion of the reaction, a plurality of peaks appeared in the range of from −90 ppm to −80 ppm. From the above, the number of Si in the molecule was considered to be 2 to 4.

A structure of the silicon oligomer determined by the above NMR measurements is such that, in the formula (I), $R_1$ to $R_{10}$ are an ethyl group, $X_1$ to $X_3$ are a group represented by the formula (II), n is 0 or 1, and m is an integer of 1 to 3 when n is 0, and m is 1 when n is 1, wherein, in the formula (II), A is an ethylene group, and l is 1.

Example 2

Preparation of a Silicon Oligomer:

A silicon oligomer was prepared in substantially the same manner as in Example 1 except that the amount of ethylene glycol was changed to 83.9 g (1.35 mol).

Before the reaction, TEOS and ethylene glycol were not mixed with each other and suffered separation into two layers. Also after the reaction, the unreacted TEOS remained as the upper layer to cause separation into two layers. This means that the degree of reaction of TEOS is low.

However, from the fact that a film was able to be formed from the separated lower layer liquid by calcining it, it has been found that, although the yield was low, a silicon oligomer having the same structure as that in Example 1 was obtained.

Example 3

Preparation of a Silicon Oligomer:

A silicon oligomer was prepared in substantially the same manner as in Example 1 except that the amount of ethylene glycol was changed to 177.8 g (2.7 mol).

Before the reaction, TEOS and ethylene glycol were not mixed with each other and suffered separation into two layers. Also after the reaction, the unreacted TEOS remained as the upper layer to cause separation into two layers. This means that the degree of reaction of TEOS is low.

However, from the fact that a film was able to be formed from the separated lower layer liquid by calcining it, it has been found that, although the yield was low, a silicon oligomer having the same structure as that in Example 1 was obtained.

Example 4

Preparation of a Silicon Oligomer:

A silicon oligomer was prepared in substantially the same manner as in Example 1 except that the amount of aluminum chloride hexahydrate was changed to 18 g.

Before the reaction, TEOS and ethylene glycol were not mixed with each other and suffered separation into two layers, but, after the reaction, they were changed to a single layer because TEOS was completely reacted. This means that the degree of reaction of TEOS is 100%.

Example 5

Preparation of a Silicon Oligomer:

A silicon oligomer was prepared in substantially the same manner as in Example 1 except that 1.8 g of aluminum chloride hexahydrate was changed to 0.93 g of cobalt chloride hexahydrate.

Before the reaction, TEOS and ethylene glycol were not mixed with each other and suffered separation into two layers, but, after the reaction, they were changed to a single layer because TEOS was completely reacted. This means that the degree of reaction of TEOS is 100%.

Example 6

Preparation of a Silicon Oligomer:

A silicon oligomer was prepared in substantially the same manner as in Example 1 except that 1.8 g of aluminum chloride hexahydrate was changed to 0.64 g of titanium trichloride.

Before the reaction, TEOS and ethylene glycol were not mixed with each other and suffered separation into two layers, but, after the reaction, they were changed to a single layer because TEOS was completely reacted. This means that the degree of reaction of TEOS is 100%.

Example 7

Preparation of a Silicon Oligomer:

A silicon oligomer was prepared in substantially the same manner as in Example 1 except that 1.8 g of aluminum chloride hexahydrate was changed to 0.8 g of hydrochloric acid.

Before the reaction, TEOS and ethylene glycol were not mixed with each other and suffered separation into two layers, but, after the reaction, they were changed to a single layer because TEOS was completely reacted. This means that the degree of reaction of TEOS is 100%.

Comparative Example 1

Preparation of a Silicon Oligomer:

A silicon oligomer was prepared in substantially the same manner as in Example 1 except that the ethylene glycol was changed to 336 g of water.

Before the reaction. TEOS and water were not mixed with each other and suffered separation into two layers, but, after the reaction, they were changed to a single layer because TEOS was completely reacted. This means that the degree of reaction of TEOS is 100%.

Test Example 1

Stability Test:

The silicon oligomers prepared in Examples 1 and 4 to 7 and Comparative Example 1 were individually diluted with ethyl cellosolve so that each silicon oligomer content became 10% to prepare diluted solutions, or the silicon oligomer prepared in Example 1 was diluted individually with polyethylene glycols of various types so that each silicon oligomer content became 10% to prepare diluted solutions. Further, these diluted solutions were individually diluted with water into a 1/2 concentration to obtain test solutions (having a silicon oligomer content of 5%). Each of the obtained test solutions was placed in a glass container and stored at room temperature. After the start of storage, each test solution was observed day by day until a change occurred. The results of the observation are shown in Table 1.

TABLE 1

| Silicon oligomer | Diluting solvent | Stability |
| --- | --- | --- |
| Example 1 | Ethyl cellosolve | Solidified after 1 month |
| | PEG200 | Solidified after 3 months |
| | PEG400 | Solidified after 2 months |
| | PEG1000 | Solidified after 2 months |
| Example 4 | Ethyl cellosolve | Solidified after 1 month |
| Example 5 | | Solidified after 1 month |
| Example 6 | | Solidified after 1 month |
| Example 7 | | Solidified after 1 week |
| Comparative Example 1 | | Solidified after 3 days |

It has been found that, as compared to an oligomer obtained from general hydrolysis of TEOS, the silicon oligomer of the invention has excellent stability for liquid. Further, it has been found that when diluted with a glycol solvent, the silicon oligomer of the invention is further improved in the stability.

Test Example 2

Film Forming Properties Test:

Diluted solutions, which had been prepared by individually diluting the silicon oligomers prepared in Examples 1 and 4 to 7 and Comparative Example 1 with ethyl cellosolve so that each silicon oligomer content became 10%, or diluted solutions, which had been prepared by diluting the silicon oligomer prepared in Example 1 individually with polyethylene glycols of various types so that each silicon oligomer content became 10%, were individually applied to M8 bolts which had been subjected to known zinc plating and then subjected to known trivalent chromium chemical conversion treatment, and the resultant bolts were calcined at 180° C. for 20 minutes. After the calcination, the resultant film was freely evaluated in respect of the appearance (film forming properties). The results of the evaluation are shown in Table 2.

TABLE 2

| Silicon oligomer | Diluting solvent | Film forming properties |
| --- | --- | --- |
| Example 1 | Ethyl cellosolve | Transparent film is formed |
| | PEG200 | Transparent film is formed |
| | PEG400 | Transparent film is formed |
| | PEG1000 | Transparent film is formed |
| Example 4 | Ethyl cellosolve | Transparent film is formed |
| Example 5 | | Opaque film is formed |
| Example 6 | | Transparent film is formed |
| Example 7 | | Transparent film is formed |
| Comparative Example 1 | | Cracks caused |

The results have confirmed that, as compared to an oligomer obtained from general hydrolysis of TEOS, the silicon oligomer of the invention has excellent film forming properties.

Test Example 3

Corrosion Resistance Test:

A commercially available bolt was subjected to zinc plating and then subjected to chemical conversion treatment (Trivalent 1200, manufactured by JCU Corporation). The resultant bolt was immersed individually in diluted solutions which had been prepared by diluting the silicon oligomers prepared in Examples 1 and 4 to 7 and Comparative Example 1 individually with ethyl cellosolve so that each silicon oligomer content became 10%, or diluted solutions which had been prepared by diluting the silicon oligomer prepared in Example 1 individually with polyethylene glycols of various types so that each silicon oligomer content became 10%, and subjected to centrifuging, and then calcined at 180° C. for 20 minutes. With respect to the resultant bolts, a salt spray test was conducted for 240 hours. The salt spray test was conducted in accordance with JIS Z 2371. With respect to the bolts obtained after the salt spray test, a white rust generation area was visually measured. The results are shown in Table 3.

TABLE 3

| Silicon oligomer | Diluting solvent | White rust generation area (%) |
|---|---|---|
| Example 1 | Ethyl cellosolve | 3 |
|  | PEG200 | 3 |
|  | PEG400 | 3 |
|  | PEG1000 | 3 |
| Example 4 | Ethyl cellosolve | 1 |
| Example 5 |  | 3 |
| Example 6 |  | 1 |
| Example 7 |  | 5 |
| Comparative Example 1 |  | 10 |

In the polymerization product of an oligomer obtained from general hydrolysis of TEOS, corrosion caused at the cracks generated was found. On the other hand, it has been found that the polymerization product of the silicon oligomer of the invention achieves high rust preventive effect. Further, it has been found that when the concentration of the catalyst (aluminum chloride) added for producing the silicon oligomer of the invention is higher, high corrosion resistance can be obtained.

Example 8

Preparation of a Coating Agent:
The silicon oligomer prepared in Example 1 was dissolved in an alkyl methacrylate copolymer (NIKASOL PK8012P, manufactured by Nippon Carbide Industries Co., Inc.) so that the silicon oligomer content became 3% to prepare a coating agent.

Example 9

Preparation of a Coating Agent:
The silicon oligomer prepared in Example 1 was dissolved in a colloidal silica-acryl composite (Newcoat PM-3101-01, manufactured by Shin-Nakamura Chemical Co., Ltd.) so that the silicon oligomer content became 3% to prepare a coating agent.

Example 10

Preparation of a Coating Agent:
The silicon oligomer prepared in Example 1 was dissolved in an ethylene-acrylic acid copolymer ammonium salt (ZAIKTHENE N, manufactured by Sumitomo Seika Chemicals Co., Ltd.) so that the silicon oligomer content became 3% to prepare a coating agent.

Test Example 4

Stability Test:
Each of the coating agents prepared in Examples 8 to 10 was placed in a glass container and stored at room temperature. After the start of storage, each coating agent was observed day by day until a change occurred. The results of the observation are shown in Table 4.

TABLE 4

| Coating agent | State of liquid |
|---|---|
| Example 8 | No change |
| Example 9 | No change |
| Example 10 | No change |

It has been found that the silicon oligomer prepared in Example 1 is stable in each of the resins in Examples 8 to 10.

Example 11

Preparation of a Coating Agent:
The silicon oligomer prepared in Example 1, an alkyl methacrylate copolymer (NIKASOL PK8012P, manufactured by Nippon Carbide Industries Co., Inc.), polyethylene glycol 200, and isopropyl alcohol were dissolved in water so that the silicon oligomer content became 3%, the copolymer content became 7%, the polyethylene glycol content became 1%, and the isopropyl alcohol content became 20% to prepare a coating agent.

Example 12

Preparation of a Coating Agent:
The silicon oligomer prepared in Example 1, a colloidal silica-acryl composite (Newcoat PM-3101-01, manufactured by Shin-Nakamura Chemical Co., Ltd.), polyethylene glycol 200, and isopropyl alcohol were dissolved in water so that the silicon oligomer content became 3%, the composite content became 7%, the polyethylene glycol content became 1%, and the isopropyl alcohol content became 20% to prepare a coating agent.

Example 13

Preparation of a Coating Agent:
The silicon oligomer prepared in Example 1, an ethylene-acrylic acid copolymer ammonium salt (ZAIKTHENE N, manufactured by Sumitomo Seika Chemicals Co., Ltd.), polyethylene glycol 200, and isopropyl alcohol were dissolved in water so that the silicon oligomer content became 3%, the copolymer ammonium salt content became 7%, the polyethylene glycol content became 1%, and the isopropyl alcohol content became 20% to prepare a coating agent.

Test Example 5

Film Forming Properties Test:
The coating agents prepared in Examples 11 to 13 were individually applied to a SUS 304 test piece (1 dm$^2$), and calcined at 180° C. for 20 minutes. After the calcination, the resultant film was freely evaluated in respect of the appearance (film forming properties). For comparison, a similar test was conducted with respect to a coating agent containing solely an alkyl methacrylate copolymer which is the resin component of the coating agent. The results are shown in Table 5.

TABLE 5

| Coating agent | Film forming properties |
| --- | --- |
| Example 11 | High transparency |
| Example 12 | Opaque film is formed |
| Example 13 | High transparency |
| Alkyl methacrylate copolymer | Transparent film is formed. Cracks caused at breakage portion |

In the coating agent containing solely the resin component, cracks were seen at the breakage portion upon forming a film, whereas, in the coating agent using the resin component and the silicon oligomer of the invention in combination, an improvement was seen in the physical properties of the film.

Test Example 6

Evaluation of a Fastening Member:
(1) Coating
A commercially available bolt with flange was subjected to zinc plating and then subjected to chemical conversion treatment (Trivalent 1200, manufactured by JCU Corporation). The resultant bolt was immersed in the coating agent prepared in Example 11, and subjected to centrifuging, and then calcined at 180° C. for 20 minutes. For purpose of comparison, a bolt having no coating agent and a bolt coated with solely an alkyl methacrylate copolymer which is the resin component of the coating agent prepared in Example 11 were prepared.
(2) Corrosion Resistance Test
With respect to the bolts obtained in the above item (1), a salt spray test and evaluation thereof were conducted in the same manner as in Test Example 3. The results of the evaluation are shown in Table 6.
(3) Measurement of a Coefficient of Friction
With respect to the bolts obtained in the above item (1), using an apparatus for measuring a coefficient of friction (manufactured by Iwata Machinery Works Ltd.), evaluation of a coefficient of friction was conducted under the conditions shown below. The results of the evaluation are shown in Table 6.
<Conditions for the Measurement of a Coefficient of Friction>
Test bolt: Bolt with flange
Test speed: 3 to 10 rpm
Fastening method: Specified axial force method
Total torque for measurement: 50 to 90 N·m
Axial force for measurement: 20 to 30 kN (Specified axial force stopped)
Torque for bolt portion measured: Not specified
Motor output: 1.5 kW

TABLE 6

| Coating agent | Corrosion resistance (%) | Coefficient of friction |
| --- | --- | --- |
| Example 11 | 1 | μ = 0.33 to 0.35 |
| Alkyl methacrylate copolymer | 50 | μ = 0.32 to 0.42 |
| None | 70 | μ = 0.26 to 0.32 |

In the case of applying no coating agent or in the case of the coating agent containing solely the resin component, the corrosion resistance was markedly poor, whereas, in the coating agent using the resin component and the silicon oligomer of the invention in combination, a remarkable improvement was seen in the corrosion resistance. Further, the coating agent using the resin component and the silicon oligomer of the invention in combination was suppressed in the dispersion of the coefficient of friction.

Test Example 7

Ductility and Malleability Check Test:
A commercially available bolt with flange was subjected to zinc plating and then subjected to chemical conversion treatment (Trivalent 1200, manufactured by JCU Corporation). The resultant bolt was immersed in a diluted solution prepared by diluting the silicon oligomer prepared in Example 4 with ethyl cellosolve so that the solids content became 20%, or in the coating agent prepared in Example 11, and subjected to centrifuging, and then calcined at 180° C. for 20 minutes. With respect to the resultant bolts, a fastening test was conducted by means of the apparatus for measuring a coefficient of friction (manufactured by Iwata Machinery Works Ltd.) used in the Test Example 6 (3), and the state of the film at the contact portion between the flange and the bearing surface after fastening was visually evaluated. For comparison, a similar test was conducted with respect to a coating agent (JN1710, manufactured by JCU-Nanomate Co., Ltd.) containing a silicon oligomer (polysiloxane) having a small distance between the poles of silicon structures. The results are shown in Table 7.

TABLE 7

| Coating agent | State of back surface of flange |
| --- | --- |
| Example 4 (Diluted solution) | Remaining film confirmed (Remaining film area 100%) |
| Example 11 | Remaining film confirmed (Remaining film area 100%) |
| JN1710 | Shattered film confirmed (Remaining film area 10%) |

With respect to the coating agent containing a silicon oligomer having a small distance between the poles of silicon structures, the film was shattered upon fastening. On the other hand, it has been found that, by using the coating agent in Example 4 or Example 11, the film suffers no shattering.

Example 12

Preparation of a Silicon Oligomer:
A silicon oligomer was prepared in substantially the same manner as in Example 1 except that the ethylene glycol was changed to 810.9 g (5.4 mol) of triethylene glycol. With respect to the obtained silicon oligomer, before the reaction, TEOS and triethylene glycol were not mixed with each other and suffered separation into two layers, but, after the reaction, they were changed to a single layer because TEOS was completely reacted. This means that the degree of reaction of TEOS is 100%. Further, from the fact that a film was able to be formed from the silicon oligomer by calcining it, it is considered that the obtained silicon oligomer is a polymerizable product like Example 1.

The obtained silicon oligomer has a structure such that, in the formula (I), $R_1$ to $R_{10}$ are an ethyl group, $X_1$ to $X_3$ are a group represented by the formula (II), n is 0 or 1, and m is an integer of 1 to 3 when n is 0, and m is 1 when n is 1, wherein, in the formula (II), A is an ethylene group, and 1 is 3.

Example 13

Preparation of a Silicon Oligomer:

A silicon oligomer was prepared in substantially the same manner as in Example 1 except that the ethylene glycol was changed to 486.6 g (5.4 mol) of 1,3-butylene glycol. With respect to the obtained silicon oligomer, before the reaction, TEOS and 1,3-butylene glycol were not mixed with each other and suffered separation into two layers, but, after the reaction, they were changed to a single layer because TEOS was completely reacted. This means that the degree of reaction of TEOS is 100%. Further, from the fact that a film was able to be formed from the silicon oligomer by calcining it, it is considered that the obtained silicon oligomer is a polymerizable product like Example 1.

The obtained silicon oligomer has a structure such that, in the formula (I), $R_1$ to $R_{10}$ are an ethyl group, $X_1$ to $X_3$ are a group represented by the formula (II), n is 0 or 1, and m is an integer of 1 to 3 when n is 0, and m is 1 when n is 1, wherein, in the formula (II), A is a methylpropylene group, and l is 1.

Example 14

Preparation of a silicon oligomer:

A silicon oligomer was prepared in substantially the same manner as in Example 1 except that the tetraethoxysilane was changed to 411.1 g (2.7 mol) of tetramethoxysilane. With respect to the obtained silicon oligomer, before the reaction, tetramethoxysilane and ethylene glycol were not mixed with each other and suffered separation into two layers, but, after the reaction, they were changed to a single layer because tetramethoxysilane was completely reacted. This means that the degree of reaction of tetramethoxysilane is 100%. Further, from the fact that a film was able to be formed from the silicon oligomer by calcining it, it is considered that the obtained silicon oligomer is a polymerizable product like Example 1.

The obtained silicon oligomer has a structure such that, in the formula (I), $R_1$ to $R_{10}$ are a methyl group, $X_1$ to $X_3$ are a group represented by the formula (II), n is 0 or 1, and m is an integer of 1 to 3 when n is 0, and m is 1 when n is 1, wherein, in the formula (II), A is an ethylene group, and l is 1.

Example 15

Preparation of a silicon oligomer:

A silicon oligomer was prepared in substantially the same manner as in Example 1 except that the tetraethoxysilane was changed to 865.5 g (2.7 mol) of tetrabutoxysilane. With respect to the obtained silicon oligomer, before the reaction, tetrabutoxysilane and ethylene glycol were not mixed with each other and suffered separation into two layers, but, after the reaction, they were changed to a single layer because tetrabutoxysilane was completely reacted. This means that the degree of reaction of tetrabutoxysilane is 100%. Further, from the fact that a film was able to be formed from the silicon oligomer by calcining it, it is considered that the obtained silicon oligomer is a polymerizable product like Example 1.

The obtained silicon oligomer has a structure such that, in the formula (I), $R_1$ to $R_{10}$ are a butyl group, $X_1$ to $X_3$ are a group represented by the formula (II), n is 0 or 1, and m is an integer of 1 to 3 when n is 0, and m is 1 when n is 1, wherein, in the formula (II), A is an ethylene group, and l is 1.

INDUSTRIAL APPLICABILITY

The silicon oligomer of the invention can be used like a conventionally known silicon oligomer in applications of a surface treatment agent and the like.

Particularly, when the silicon oligomer of the invention is used in a coating agent, the resultant coating agent can form a film having flexibility, and therefore can be advantageously used in coating for a fastening member and the like.

The invention claimed is:

1. A coating agent comprising a silicon oligomer represented by the following formula (I):

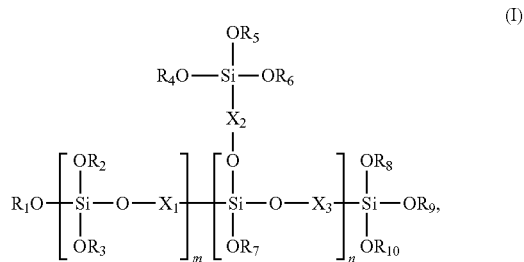

wherein $R_1$ to $R_{10}$ each independently is an alkyl group or a hydroxyalkyl group, each having 1 to 4 carbon atoms; $X_1$ to $X_3$ each independently is a group represented by the following formula (II); n is 0 or 1; and m is an integer of 1 to 3 when n is 0, and m is 1 when n is 1:

wherein A is an alkylene group having 2 to 4 carbon atoms, which may be branched, and l is an integer of 1 to 3, and the silicon oligomer of the formula (I) is obtained by reacting a tetraalkoxysilane represented by the following formula (III):

wherein $R_{11}$ to $R_{14}$ each independently is an alkyl group or a hydroxyalkyl group, each having 1 to 4 carbon atoms, and a dihydric alcohol represented by the following formula (IV):

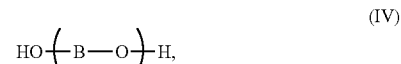

wherein B is an alkylene group having 2 to 4 carbon atoms, which may be branched, and k is an integer of 1 to 3, in the presence of a metal catalyst, and when an alcohol formed during the reaction is not subjected to fractional distillation, wherein the metal catalyst is dissolved in the dihydric alcohol forming a mixture and a tetraalkoxysilane is added to the mixture such that the tetraalkoxysilane is reacted with the dihydric alcohol in the presence of the metal catalyst, and wherein the metal catalyst comprises at least one selected from the group consisting of aluminum, cobalt, titanium, zinc, molybdenum, and tin.

2. The coating agent according to claim 1, comprising at least one selected from the group consisting of a resin, a colorant, a friction coefficient adjustor, and a film-forming agent.

3. The coating agent according to claim 2, wherein the resin is at least one selected from the group consisting of an acrylic resin, urethane resin, phenolic resin, and epoxy resin.

4. The coating agent according to claim 2, wherein the colorant is at least one selected from the group consisting of a dye colorant and pigment colorant.

5. The coating agent according to claim 2, wherein the friction coefficient adjustor is at least one member selected from the group consisting of a polyolefin compound and fluorine compound.

6. The coating agent according to claim 2, wherein the film-forming agent is at least one selected from the group consisting of colloidal silica and fumed silica.

7. The coating agent according to claim 1, wherein the dihydric alcohol represented by the formula (IV) is at least one selected from the group consisting of ethylene glycol, propylene glycol, and butylene glycol.

8. The coating agent according to claim 1, wherein a molar ratio of the tetraalkoxysilane represented by the formula (III) and the dihydric alcohol represented by the formula (IV) is 4:1 to 1:4.

9. A method for surface treatment, comprising treating a member with the coating agent according to claim 1.

10. The method for surface treatment according to claim 9, wherein the surface of the member to be treated comprises magnesium or a magnesium alloy.

11. The method for surface treatment according to claim 9, wherein the surface of the member to be treated comprises zinc or a zinc alloy.

12. The method for surface treatment according to claim 9, wherein the surface of the member to be treated comprises a metal selected from the group consisting of iron, copper, nickel, cobalt, chromium, and tin, or an alloy comprising two or more metals thereof.

13. The method for surface treatment according to claim 9, wherein the surface of the member to be treated comprises a synthetic resin selected from the group consisting of an acrylonitrile-butadiene-styrene copolymer, a polycarbonate, bismaleimidetriazine, and a polyimide, or a synthetic resin alloy comprising two or more resins thereof.

14. A surface treated product obtained by treating the surface with the coating agent according to claim 1.

15. The surface treated product according to claim 14, wherein the surface of the member to be treated comprises magnesium or a magnesium alloy.

16. The surface treated product according to claim 14, wherein the surface of the member to be treated comprises zinc or a zinc alloy.

17. The surface treated product according to claim 14, wherein the surface of the member to be treated is comprises a metal selected from the group consisting of iron, copper, nickel, cobalt, chromium, and tin, or an alloy comprising two or more metals thereof.

18. The surface treated product according to claim 14, wherein the surface of the member to be treated comprises a synthetic resin selected the group consisting of an acrylonitrile-butadiene-styrene copolymer, a polycarbonate, bismaleimidetriazine, and a polyimide, or a synthetic resin alloy comprising two or more resins thereof.

19. The coating agent of claim 1, wherein the mixture is heated to a reaction temperature of 25 to 150° C. while stirring, and then the tetraalkoxysilane is added to the mixture, wherein a reaction time of from 30 minutes to 8 hours.

20. The coating agent of claim 1, wherein the metal catalyst is a catalyst metal salt.

21. The coating agent of claim 1, wherein the metal catalyst is added to the dihydric alcohol to form the mixture and no additional catalyst is added in the reaction.

* * * * *

UNITED STATES PATENT AND TRADEMARK OFFICE
CERTIFICATE OF CORRECTION

PATENT NO. : 10,533,022 B2
APPLICATION NO. : 15/699714
DATED : January 14, 2020
INVENTOR(S) : Daisuke Sadohara et al.

It is certified that error appears in the above-identified patent and that said Letters Patent is hereby corrected as shown below:

On the Title Page

Item (56), Other Publications, Line 10, "AZ201380077750.2" should read --201380077750.2--.

In the Specification

Column 1, Line 45, "1990" should read --1990.--.

Column 3, Line 48, "$K_3$" should read --$X_3$--.

Column 5, Line 33, "$^{29}S1$" should read --$^{29}Si$--,
 Line 35, "$^{29}S1$" should read --$^{29}Si$--.

Column 9, Line 37, "reaction." should read --reaction,--.

Signed and Sealed this
Twenty-first Day of July, 2020

Andrei Iancu
*Director of the United States Patent and Trademark Office*